United States Patent
Krapchetov et al.

(10) Patent No.: US 10,745,341 B2
(45) Date of Patent: Aug. 18, 2020

(54) METHOD FOR PRODUCTION OF METHYL METHACRYLATE BY OXIDATIVE ESTERIFICATION USING A HETEROGENEOUS CATALYST

(71) Applicants: Dow Global Technologies LLC, Midland, MI (US); Rohm and Haas Company, Collegeville, PA (US)

(72) Inventors: Dmitry A. Krapchetov, Lansdale, PA (US); Kirk W. Limbach, Dresher, PA (US); Daniel A. Hickman, Midland, MI (US); Jeffrey Herron, Midland, MI (US); Kurt W. Olson, Midland, MI (US); D. Wayne Blaylock, Fort Bend, TX (US)

(73) Assignees: Dow Global Technologies LLC, Midland, MI (US); Rohm and Haas Company, Collegeville, PA (US)

( * ) Notice: Subject to any disclaimer, the term of this patent is extended or adjusted under 35 U.S.C. 154(b) by 0 days.

(21) Appl. No.: 16/634,752

(22) PCT Filed: Jun. 25, 2018

(86) PCT No.: PCT/US2018/039231
§ 371 (c)(1),
(2) Date: Jan. 28, 2020

(87) PCT Pub. No.: WO2019/022886
PCT Pub. Date: Jan. 31, 2019

(65) Prior Publication Data
US 2020/0199059 A1 Jun. 25, 2020

Related U.S. Application Data

(60) Provisional application No. 62/538,232, filed on Jul. 28, 2017.

(51) Int. Cl.
| | | |
|---|---|---|
| *C07C 67/44* | (2006.01) | |
| *B01J 35/02* | (2006.01) | |
| *B01J 23/52* | (2006.01) | |
| *B01J 23/44* | (2006.01) | |
| *B01J 8/06* | (2006.01) | |
| *B01J 8/04* | (2006.01) | |
| *C07C 45/75* | (2006.01) | |
| *C07C 69/54* | (2006.01) | |

(52) U.S. Cl.
CPC ............ *C07C 67/44* (2013.01); *B01J 8/0492* (2013.01); *B01J 8/065* (2013.01); *B01J 8/067* (2013.01); *B01J 23/44* (2013.01); *B01J 23/52* (2013.01); *B01J 35/023* (2013.01); *C07C 45/75* (2013.01); *C07C 69/54* (2013.01); *B01J 2208/0053* (2013.01); *B01J 2208/00106* (2013.01); *B01J 2208/00592* (2013.01)

(58) Field of Classification Search
CPC ......... C07C 67/39; C07C 45/75; C07C 69/54; B01J 23/89; B01J 23/44
See application file for complete search history.

(56) References Cited

U.S. PATENT DOCUMENTS

| | | |
|---|---|---|
| 4,249,019 A | 2/1981 | Tamura et al. |
| 4,518,796 A | 5/1985 | Aoshima et al. |
| 4,520,125 A | 5/1985 | Baer et al. |
| 5,892,102 A | 4/1999 | Mikami et al. |
| 5,969,178 A | 10/1999 | Okamoto et al. |
| 6,040,472 A | 3/2000 | Yamamatsu et al. |
| 6,228,800 B1 | 5/2001 | Yamaguchi et al. |
| 7,326,806 B2 | 2/2008 | Hayashi et al. |
| 8,461,373 B2 | 6/2013 | Suzuki et al. |
| 8,614,349 B2 | 12/2013 | Yokota et al. |
| 9,511,351 B2 | 12/2016 | Feaviour |
| 9,617,199 B2 | 4/2017 | Krill et al. |
| 2016/0251301 A1 | 9/2016 | Krill et al. |
| 2016/0280628 A1 | 9/2016 | Krill et al. |
| 2019/0099731 A1* | 4/2019 | Lygin ...................... B01J 8/226 |

FOREIGN PATENT DOCUMENTS

| | | |
|---|---|---|
| CN | 1931824 A | 3/2007 |
| JP | 2003048863 A | 2/2003 |
| WO | 2015091173 | 6/2015 |
| WO | 2017084969 | 5/2017 |

* cited by examiner

*Primary Examiner* — Jafar F Parsa
(74) *Attorney, Agent, or Firm* — Brian L. Mutschler

(57) ABSTRACT

A method for preparing methyl methacrylate from methacrolein and methanol. The method comprises contacting in a tubular reactor having at least four zones a mixture comprising methacrolein, methanol, oxygen and a base with a catalyst bed of heterogeneous catalyst comprising a support and a noble metal, wherein reaction zones comprising catalyst beds alternate with mixing zones not comprising catalyst beds.

10 Claims, No Drawings

METHOD FOR PRODUCTION OF METHYL METHACRYLATE BY OXIDATIVE ESTERIFICATION USING A HETEROGENEOUS CATALYST

BACKGROUND OF THE INVENTION

The invention relates to a method for preparing methyl methacrylate from methacrolein and methanol using a heterogeneous catalyst.

Methyl methacrylate has been produced by oxidative esterification reactions in which decreases in pH of the reaction mixture are known to be detrimental. The prior art reports that addition of base to the reactor to raise pH is done to increase catalyst life. The solution to this problem has been to mix the base into a portion of the reaction mixture or reactants in a separate vessel, see, e.g., U.S. Pub. No. 2016/0251301. However, there is a need for a more efficient process which can provide improved selectivity.

SUMMARY OF THE INVENTION

The present invention is directed to a method for preparing methyl methacrylate from methacrolein and methanol; said method comprising contacting in a tubular reactor comprising at least four zones a mixture comprising methacrolein, methanol, oxygen and a base with a catalyst bed of heterogeneous catalyst comprising a support and a noble metal, wherein reaction zones comprising catalyst beds alternate with mixing zones not comprising catalyst beds.

DETAILED DESCRIPTION OF THE INVENTION

All percentage compositions are weight percentages (wt %), and all temperatures are in ° C., unless otherwise indicated. Averages are arithmetic averages unless otherwise indicated. A noble metal is any of gold, platinum, iridium, osmium, silver, palladium, rhodium and ruthenium. More than one noble metal may be present in the catalyst, in which case the limits apply to the total of all noble metals. The "catalyst center" is the centroid of the catalyst particle, i.e., the mean position of all points in all coordinate directions. A diameter is any linear dimension passing through the catalyst center and the average diameter is the arithmetic mean of all possible diameters. The aspect ratio is the ratio of the longest to the shortest diameters. A "zone" is a portion of the length of a tubular reactor, i.e., a reactor having a substantially circular cross-section in which a reaction mixture flows along the length (central axis) of the reactor perpendicular to the cross section. The length of a zone is its dimension along the central axis of the reactor. The tubular reactor is operated as a continuous reactor.

Preferably, the first zone is a mixing zone into which fresh reactants are fed. Preferably, base is also fed to the first mixing zone, either with the reactants or separately. In a preferred embodiment of the invention, base, oxygen or both are fed to at least one subsequent mixing zone as well as the first mixing zone. Preferably, a portion of the reaction mixture is recycled to the first mixing zone from subsequent mixing zones. Preferably, the reactor has at least four mixing zones, preferably at least three, preferably at least two; preferably no more than ten preferably no more than five. Preferably a ratio of the average length of the reaction zones to the average length of the mixing zones is from 1000:1 to 1:5, preferably 500:1 to 1:2, preferably 100:1 to 1:1. Preferably a ratio of the average length of all zones to the reactor diameter is from 1000:1 to 1:10, preferably 500:1 to 1:5, preferably 100:1 to 1:2. Zones need not be the same length. Preferably, the reactor is substantially vertical with upward flow of reaction mixture and gases.

Preferably, the reactor comprises at least one cooling zone in which heat is removed from the reaction mixture passing through the zone. A mixing zone may also be a cooling zone. Preferably, cooling is accomplished by contacting the reaction mixture with a heat exchanger which may comprise coils, fins, or other typical heat exchange surfaces.

Preferred bases include alkali metal hydroxides and $C_1$-$C_4$ alkoxides, preferably sodium and potassium hydroxide and sodium or potassium methoxide or ethoxide, preferably sodium hydroxide or sodium methoxide. Preferably, base is added as a solution, preferably in methanol, ethanol or water; preferably methanol or water. Preferably, alkoxides are added in methanol or ethanol. Preferably, the concentration of base in the solution is from 50 to 1 wt %, preferably from 45 to 2 wt %, preferably from 40 to 5 wt %.

Preferably, reaction mixture in a mixing zone is mixed using a static mixing device, mechanical agitation or jet mixing. Preferably, mechanical agitation is accomplished using one or more impellers. Preferably, impellers have a tip speed from 0.1 to 10 m/s; preferably from 1 to 5 m/s. Preferably the mixing zone contains a heat exchange device for cooling or heating purposes.

Preferably, superficial velocity of liquid through the catalyst beds is from 1 to 100 mm/s; preferably at least 2 mm/s, preferably at least 3 mm/s, preferably at least 5 mm/s; preferably no greater than 30 mm/s, preferably no greater than 25 mm/s, preferably no greater than 20 mm/s. Preferably, the mixing zones have at least one impeller per reactor diameter. Preferably, the linear tip speed of the impeller is from 0.1 to 10 m/s; preferably at least 0.2 m/s, preferably at least 0.5 m/s, preferably at least 1 m/s, preferably at least 2 m/s; preferably no greater than 8 m/s, preferably no greater than 6 m/s. Preferably, the specific energy dissipation, ε is from 0 to 5 W/kg; preferably at least 0.5 W/kg, preferably at least 1.0 W/kg; preferably no more than 4 W/kg, preferably no more than 3.5 W/kg. Preferably, H/T for the reactor is at least 1.2, preferably at least 1.3, preferably at least 1.4; preferably no greater than 5, preferably no greater than 4, preferably no greater than 3.

Preferably, oxygen concentration at a reactor outlet is from 0.5 to 7.5 mol %; preferably at least 1 mol %; preferably no greater than 6 mol %.

Preferably, the support is a particle of an oxide material; preferably γ-, δ-, or θ-alumina, silica, magnesia, titania, zirconia, hafnia, vanadia, niobium oxide, tantalum oxide, ceria, yttria, lanthanum oxide or a combination thereof. Preferably, in portions of the catalyst comprising the noble metal, the support has a surface area greater than 10 $m^2$/g, preferably greater than 30 $m^2$/g, preferably greater than 50 $m^2$/g, preferably greater than 100 $m^2$/g, preferably greater than 120 $m^2$/g. In portions of the catalyst which comprise little or no noble metal, the support may have a surface area less than 50 $m^2$/g, preferably less than 20 $m^2$/g.

Preferably, the aspect ratio of the catalyst particle is no more than 10:1, preferably no more than 5:1, preferably no more than 3:1, preferably no more than 2:1, preferably no more than 1.5:1, preferably no more than 1.1:1. Preferred shapes for the catalyst particle include spheres, cylinders, rectangular solids, rings, multi-lobed shapes (e.g., cloverleaf cross section), shapes having multiple holes and "wagon wheels;" preferably spheres. Irregular shapes may also be used.

Preferably, at least 90 wt % of the noble metal(s) is in the outer 70% of catalyst volume (i.e., the volume of an average catalyst particle), preferably the outer 60% of catalyst volume, preferably the outer 50%, preferably the outer 40%, preferably the outer 35%, preferably in the outer 30%, preferably in the outer 25%. Preferably, the outer volume of any particle shape is calculated for a volume having a constant distance from its inner surface to its outer surface (the surface of the particle), measured along a line perpendicular to the outer surface. For example, for a spherical particle the outer x % of volume is a spherical shell whose outer surface is the surface of the particle and whose volume is x % of the volume of the entire sphere. Preferably, at least 95 wt % of the noble metal is in the outer volume of the catalyst, preferably at least 97 wt %, preferably at least 99 wt %. Preferably, at least 90 wt % (preferably at least 95 wt %, preferably at least 97 wt %, preferably at least 99 wt %) of the noble metal(s) is within a distance from the surface that is no more than 30% of the catalyst diameter, preferably no more than 25%, preferably no more than 20%, preferably no more than 15%, preferably no more than 10%, preferably no more than 8%. Distance from the surface is measured along a line which is perpendicular to the surface.

Preferably, the noble metal is gold or palladium, preferably gold.

Preferably, the average diameter of the catalyst particle is at least 200 microns, preferably at least 300 microns, preferably at least 400 microns, preferably at least 500 microns, preferably at least 600 microns, preferably at least 700 microns, preferably at least 800 microns; preferably no more than 30 mm, preferably no more than 20 mm, preferably no more than 10 mm, preferably no more than 5 mm, preferably no more than 4 mm, preferably no more than 3 mm. The average diameter of the support and the average diameter of the final catalyst particle are not significantly different.

Preferably, the catalyst is produced by precipitating the noble metal from an aqueous solution of metal salts in the presence of the support. Preferred noble metal salts include tetrachloroauric acid, sodium aurothiosulfate, sodium aurothiomalate, gold hydroxide, palladium nitrate, palladium chloride and palladium acetate. In one preferred embodiment, the catalyst is produced by an incipient wetness technique in which an aqueous solution of a suitable noble metal precursor salt is added to a porous inorganic oxide such that the pores are filled with the solution and the water is then removed by drying. The resulting material is then converted into a finished catalyst by calcination, reduction, or other treatments known to those skilled in the art to decompose the noble metal salts into metals or metal oxides. Preferably, a $C_2$-$C_{18}$ thiol comprising at least one hydroxyl or carboxylic acid substituent is present in the solution. Preferably, the $C_2$-$C_{15}$ thiol comprising at least one hydroxyl or carboxylic acid substituent has from 2 to 12 carbon atoms, preferably 2 to 8, preferably 3 to 6. Preferably, the thiol compound comprises no more than 4 total hydroxyl and carboxylic acid groups, preferably no more than 3, preferably no more than 2. Preferably, the thiol compound has no more than 2 thiol groups, preferably no more than one. If the thiol compound comprises carboxylic acid substituents, they may be present in the acid form, conjugate base form or a mixture thereof. The thiol component also may be present either in its thiol (acid) form or its conjugate base (thiolate) form. Especially preferred thiol compounds include thiomalic acid, 3-mercaptopropionic acid, thioglycolic acid, 2-mercaptoethanol and 1-thioglycerol, including their conjugate bases.

In one embodiment of the invention, the catalyst is produced by deposition precipitation in which a porous inorganic oxide is immersed in an aqueous solution containing a suitable noble metal precursor salt and that salt is then made to interact with the surface of the inorganic oxide by adjusting the pH of the solution. The resulting treated solid is then recovered (e.g. by filtration) and then converted into a finished catalyst by calcination, reduction, or other pre-treatments known to those skilled in the art to decompose the noble metal salts into metals or metal oxides.

This invention is useful in a process for producing methyl methacrylate (MMA) which comprises treating methacrolein with methanol in an oxidative esterification reactor (OER) containing catalyst beds. The catalyst beds comprise the catalyst particles. The OER further comprises a liquid phase comprising methacrolein, methanol and MMA and a gaseous phase comprising oxygen. The liquid phase may further comprise byproducts, e.g., methacrolein dimethyl acetal (MDA) and methyl isobutyrate (MIB). Preferably, the liquid phase is at a temperature from 40 to 120° C.; preferably at least 50° C., preferably at least 60° C.; preferably no more than 110° C., preferably no more than 100° C. Preferably, the catalyst bed is at a pressure from 0 to 2000 psig (101 kPa to 14 MPa); preferably no more than 2000 kPa, preferably no more than 1500 kPa. Preferably, pH in the catalyst bed is from 4 to 10; preferably at least 5, preferably at least 5.5; preferably no greater than 9, preferably no greater than 8, preferably no greater than 7.5. Preferably, the catalyst bed is in a tubular continuous reactor.

The OER typically produces MMA, along with methacrylic acid and unreacted methanol. Preferably, methanol and methacrolein are fed to the reactor in a methanol: methacrolein molar ratio from 1:10 to 100:1, preferably from 1:2 to 20:1, preferably from 1:1 to 10:1. Preferably, a catalyst bed further comprises inert materials. Preferred inert materials include, e.g., alumina, clay, glass, silica carbide and quartz. Preferably, the inert materials located before and/or after the catalyst bed have an average diameter equal to or greater than that of the catalyst, preferably 1 to 30 mm; preferably at least 2 mm; preferably no greater than 30 mm, preferably no greater than 10 mm, preferably no greater than 7 mm Preferably, the reaction products are fed to a methanol recovery distillation column which provides an overhead stream rich in methanol and methacrolein; preferably this stream is recycled back to the OER. The bottoms stream from the methanol recovery distillation column comprises MMA, MDA, methacrylic acid, salts and water. In one embodiment of the invention, MDA is hydrolyzed in a medium comprising MMA, MDA, methacrylic acid, salts and water. MDA may be hydrolyzed in the bottoms stream from a methanol recovery distillation column; said stream comprising MMA, MDA, methacrylic acid, salts and water. In another embodiment, MDA is hydrolyzed in an organic phase separated from the methanol recovery bottoms stream. It may be necessary to add water to the organic phase to ensure that there is sufficient water for the MDA hydrolysis; these amounts may be determined easily from the composition of the organic phase. The product of the MDA hydrolysis reactor is phase separated and the organic phase passes through one or more distillation columns to produce MMA product and light and/or heavy byproducts. In another embodiment, hydrolysis could be conducted within the distillation column itself.

Preferably, oxygen concentration at a reactor outlet is at least 1 mol %, preferably at least 2 mol %, preferably at least 3 mol %; preferably no more than 7 mol %, preferably no more than 6.5 mol %, preferably no more than 6 mol %.

In a preferred embodiment of the invention, pH at the reactor outlet is from 3 to 7.5; preferably at least 3.5, preferably at least 4, preferably at least 4.5, preferably at least 4.8, preferably at least 5; preferably no more than 7.3, preferably no more than 7.0, preferably no more than 6.7, preferably no more than 6.4. Preferably, base is not added to the reactor or to liquid streams entering the reactor. Preferably, the reactor is not connected to an external mixing tank through which base is introduced. pH in the reactor is likely to be higher, possibly above 7 near the inlet and dropping below 6 at the outlet.

One preferred embodiment of the fixed bed reactor for oxidative esterification is a trickle bed reactor, which contains a fixed bed of catalyst and passes both the gas and liquid feeds through the reactor in the downward direction. In trickle flow, the gas phase is the continuous fluid phase. Thus, the zone at the top of the reactor, above the fixed bed, will be filled with a vapor phase mixture of nitrogen, carbon dioxide, oxygen, and the volatile liquid components at their respective vapor pressures. Under typical operating temperatures and pressures (50-90° C. and 60-300 psig (510-2200 kPa), this vapor mixture is inside the flammable envelope if the gas feed is air. Thus, only an ignition source would be required to initiate a deflagration, which could lead to loss of primary containment and harm to the physical infrastructure and personnel in the vicinity. In order to address process safety considerations, a means to operate a trickle bed reactor while avoiding a flammable headspace atmosphere is operation with a gas feed containing a sufficiently low oxygen mole fraction to ensure the oxygen concentration in the vapor headspace is below the limiting oxygen concentration (LOC).

Knowledge of the LOC is required for the fuel mixture, temperature, and pressure of concern. Since the LOC decreases with increasing temperature and pressure, and given that methanol gives a lower LOC than the other two significant fuels (methacrolein and methyl methacrylate), a conservative design chooses a feed oxygen to inert gas ratio that ensures a composition with less than the LOC at the highest expected operating temperature and pressure. For example, for a reactor operated at up to 100° C. and 275 psig (1990 kPa), the feed oxygen concentration in nitrogen and/or carbon dioxide should not exceed 7.4 mol %. One method of obtaining the lower oxygen concentration in the reactor is recycling reactor off-gas and adding fresh air to that off-gas to bring the oxygen content up to a desired amount.

EXAMPLES

Example #1: Multi-Zone Reactor

A series of runs was conducted in which 20 wt % methacrolein, 200 ppm inhibitor, and a balance of methanol were mixed and fed to a catalytic zone consisting of ⅜" (9.5 mm) stainless steel tubular reactor containing a short front section of silica carbide and 10 g of catalyst followed by a mixing zone consisting of a 150 ml liquid volume stirred vessel with a pitched blade turbine, followed by a second catalytic zone consisting of ⅜" stainless steel tubular reactor containing a short front section of silica carbide and 10 g of catalyst. The catalyst consisted of 1.5 wt % Au on a Norpro 1 mm diameter high surface area alumina spherical support. Air was fed to the first catalyst zone sufficient to have roughly 5% oxygen in the outlet gas and a gas containing 8% oxygen in nitrogen was fed to the second zone sufficient to have an outlet gas between 4% and 5% oxygen. The reactors were operated at 60° C. and 160 psig (1200 kPa). The pH at the exit of catalyst zone 1 was approximately 6.3. The product of the reactor was sent to a liquid-vapor separator and the vapor was sent to a condenser with liquid return. Results are described in the below table. A base consisting of sodium methoxide in methanol was added to the mixing zone in some cases. The mixing zone was stirred at 600 RPM in some cases and not stirred in other cases. Product distribution for MMA is the percent MMA among products originating as methacrolein reactant. Product distribution for Michael Adducts is the percent adducts among products originating as methacrolein reactant. Space-time yield is in mol MMA per Kg catalyst hour.

| run | Base wt % NaOMe | mixing (RPM) | Feed (g/hr) | Base (g/hr) | Zone 2 Exit (pH) | Prod Dist, MMA % | Prod Dist, Adducts % | Conv (%) | STY (m/Kghr) |
|---|---|---|---|---|---|---|---|---|---|
| 1 | na | 600 | 40 | 0 | 5.8 | 97.4 | 0.3 | 67 | 3.1 |
| 2 | 3 | 600 | 40 | 2 | 7 | 97.3 | 1.2 | 88 | 3.7 |
| 3 | 3 | 0 | 40 | 2 | 7.2 | 96.4 | 2.3 | 90 | 3.7 |

Comparative Example #2: Recycle Reactor

A run was conducted in which 20 wt % methacrolein, 200 ppm inhibitor, and a balance of methanol were fed to a ⅜" stainless steel tubular reactor containing a short front section of silica carbide followed by 10 g of catalyst. The catalyst consisted of 1.5 wt % Au on a Norpro 1 mm diameter high surface area alumina spherical support. A gas containing 8 mol % oxygen in nitrogen was feed to the reactor at 300 sccm and oxygen concentration in the vent gas was between 4 mol % and 5 mol %. The reactor was operated at 60° C. and 160 psig. The product of the reactor was sent to a liquid-vapor separator and the vapor was sent to a condenser with liquid return. A portion of the product stream from this separator was recycled to the reactor inlet and combined with the feed entering the reactor. Results are described in the below table. Product distribution is the percent MMA among products originating as methacrolein reactant. A base consisting of 0.15 wt % sodium methoxide in methanol was added to the liquid-vapor separator which contained a pitch blade impeller for mixing purposes.

| Run | Feed (g/hr) | Recycle (g/hr) | Base (g/hr) | Effluent (pH) | Prod Dist (MMA %) | Prod Dist (Adducts %) | Conv (%) | STY (m/Kghr) |
|---|---|---|---|---|---|---|---|---|
| 4 | 20 | 180 | 20 | 6.8 | 93.7 | 1.1 | 60 | 2.7 |

CONCLUSIONS

Data obtained in the multi-zone reactor indicates that for base addition to the reactor, mixing in the mixing zone(s) is an important parameter to decrease the formation of Michael Adducts and increase selectivity in general as measured here by product distribution to MMA. Michael Adduct formation roughly doubled when improper mixing in the mixing zone was utilized vs. more typical and appropriate mixing at 600 RPM.

Comparison of the multi-zone reactor to a recycle reactor with 90% recycle, even in the case of very dilute base addition, indicates the multi-zone performance was comparable or superior to that of the recycle reactor with superior product distribution to MMA (selectivity), conversion, and space-time yield.

The invention claimed is:

1. A method for preparing methyl methacrylate from methacrolein and methanol; said method comprising contacting in a tubular reactor having at least four zones a mixture comprising methacrolein, methanol, oxygen and a base with a catalyst bed of heterogeneous catalyst comprising a support and a noble metal, wherein reaction zones comprising catalyst beds alternate with mixing zones not comprising catalyst beds.

2. The method of claim 1 in which each reaction zone comprises a catalyst bed comprising catalyst particles having an average diameter from 200 microns to 10 mm.

3. The method of claim 2 in which superficial velocity of liquid through the reactor is from 2 to 30 mm/s.

4. The method of claim 3 in which each mixing zone comprises a heat exchange device and at least one of: (i) a static mixing device, (ii) a jet mixing device, and (iii) at least one impeller having a tip speed from 0.1 to 10 m/s.

5. The method of claim 4 in which the catalyst beds are at a temperature from 40 to 120° C.

6. The method of claim 5 in which pH in the catalyst beds is from 4 to 8.

7. The method of claim 6 in which the reactor has from four to ten zones.

8. The method of claim 7 in which the base is sodium hydroxide or sodium methoxide.

9. The method of claim 8 in which the catalyst particles have an average diameter from 400 microns to 7 mm.

10. The method of claim 9 in which the noble metal is selected from the group consisting of gold and palladium.

* * * * *